(12) United States Patent
Whitaker (10) Patent No.: US 9,321,079 B2
(45) Date of Patent: Apr. 26, 2016

(54) PROCESS FOR MANUFACTURING A PLURALITY OF WAVE ENERGY EMITTERS

(71) Applicant: George Whitaker, Bloomington, IN (US)

(72) Inventor: George Whitaker, Bloomington, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 214 days.

(21) Appl. No.: 14/054,355

(22) Filed: Oct. 15, 2013

(65) Prior Publication Data

US 2014/0245596 A1 Sep. 4, 2014

Related U.S. Application Data

(60) Provisional application No. 61/713,670, filed on Oct. 15, 2012.

(51) Int. Cl.
| | |
|---|---|
| B06B 1/00 | (2006.01) |
| A61B 8/00 | (2006.01) |
| B01J 19/10 | (2006.01) |
| G10K 13/00 | (2006.01) |
| G01N 29/22 | (2006.01) |
| G08B 13/16 | (2006.01) |

(52) U.S. Cl.
CPC ... *B06B 1/00* (2013.01); *A61B 8/00* (2013.01); *B01J 19/10* (2013.01); *G01N 29/221* (2013.01); *G10K 13/00* (2013.01); *G08B 13/1609* (2013.01); *Y10T 29/49005* (2015.01)

(58) Field of Classification Search
CPC ......... H05K 3/00; H05K 13/00; H04R 31/00; H04R 31/006; A61B 8/00; B01J 19/10; B06B 1/00; G01N 29/221; G08B 13/1609; G10K 13/00; Y10T 29/49005
See application file for complete search history.

(56) References Cited

U.S. PATENT DOCUMENTS 3,021,711 A * 2/1962 Arvidson ........................ 73/702

FOREIGN PATENT DOCUMENTS

EP 0 088 362 * 9/1983

* cited by examiner

*Primary Examiner* — Carl Arbes
(74) *Attorney, Agent, or Firm* — Christopher A. Monsey (57) ABSTRACT

A process for manufacturing a wave energy emitter and a system for manufacturing the same.

7 Claims, 7 Drawing Sheets

Step 1: Calculate and create first data defining a desired fractal antenna(s) including a) defining attributes of the desired fractal antenna to include fractal order number N, b) defining a distance ratio defined as a ratio of distance travelled between an initially selected random position and an incrementally selected fractal vertices within a cirlce transcribed around all potential vertices of the desired fractal antenna; c) define potential coordinate points of the desired fractal antenna, including fractal elements, based on the defined attributes and the distance ratio.

Step 2: Determine a minimum separation distance between boundary edges of adjacent said fractal elements defined in said first data required to ensure structural integrity of the fractal elements within a substrate, where the minimum separation distance is further determined based on predetermined performance specification(s) of the fractal elements (e.g., desired frequency) as well as thickness and type of material the substrate is formed from.

Step 3: Determine coordinates of an initial plurality of potential material removal points that may be removed from the defined desired fractal antenna's fractal pattern based on the first data, the minimum separation distance, and a predetermined material removal point size or iteration number.

Continued at Fig 3B

Step 4: Determine locations of the substrate where material will be removed based on deletion of some of the initial plurality of potential material removal points which degrade mechanical integrity of the fractal antenna by determining the potential material removal points that meet at least one deletion parameter. The at least one deletion parameter is determined based on an identification of a closest potential material removal point to a selected potential material removal point. The identification of the closest material removal point is based on an iterative analysis of all said potential material removal points where each iteration determines a plurality of mean squared distances between a selected said potential material removal point and all closest potential material removal points to the selected potential material removal point, then selecting a smallest means squared distance from the plurality of means squared distances, then deleting the closest potential material removal point having the smallest mean squared distance, then repeating the determining potential removal points that meet at least one deletion parameter step until no remaining potential material removal points have a means squared distance with adjacent potential material removal points equal to or less than the minimum separation distance determined in Step 2, then Step 4 ends and a final plurality of potential material removal points.

Step 5: Iteratively starting with a starting material removal point closest to a center of a selected smallest emitting structure (e.g., fractal resonating structure), use a material removal device, such as a laser, to remove material, e.g., drill holes, around the selected smallest emitting structure in the antenna substrate, e.g., metal, based on the final plurality of potential material removal points until the smallest emitting structure, e.g., fractal antennas, emit (e.g., resonate) at a first predetermined percent, e.g., five percent, under the desired frequency associated with the emitter (e.g., fractal emitter); repeat for all same sized emitting structures as the smallest emitting structure.

Step 1: Calculate and create first data defining a desired fractal antenna(s) including a) defining attributes of the desired fractal antenna to include fractal order number N, b) defining a distance ratio defined as a ratio of distance travelled between an initially selected random position and an incrementally selected fractal vertices within a cirlce transcribed around all potential vertices of the desired fractal antenna; c) define potential coordinate points of the desired fractal antenna, including fractal elements, based on the defined attributes and the distance ratio.

Step 2: Determine a minimum separation distance between boundary edges of adjacent said fractal elements defined in said first data required to ensure structural integrity of the fractal elements within a substrate, where the minimum separation distance is further determined based on predetermined performance specification(s) of the fractal elements (e.g., desired frequency) as well as thickness and type of material the substrate is formed from.

Step 3: Determine coordinates of an initial plurality of potential material removal points that may be removed from the defined desired fractal antenna's fractal pattern based on the first data, the minimum separation distance, and a predetermined material removal point size or iteration number.

Step 4: Determine locations of the substrate where material will be removed based on deletion of some of the initial plurality of potential material removal points which degrade mechanical integrity of the fractal antenna by determining the potential material removal points that meet at least one deletion parameter. The at least one deletion parameter is determined based on an identification of a closest potential material removal point to a selected potential material removal point. The identification of the closest material removal point is based on an iterative analysis of all said potential material removal points where each iteration determines a plurality of mean squared distances between a selected said potential material removal point and all closest potential material removal points to the selected potential material removal point, then selecting a smallest means squared distance from the plurality of means squared distances, then deleting the closest potential material removal point having the smallest mean squared distance, then repeating the determining potential removal points that meet at least one deletion parameter step until no remaining potential material removal points have a means squared distance with adjacent potential material removal points equal to or less than the minimum separation distance determined in Step 2, then Step 4 ends and a final plurality of potential material removal points.

Step 5: Iteratively starting with a starting material removal point closest to a center of a selected smallest emitting structure (e.g., fractal resonating structure), use a material removal device, such as a laser, to remove material, e.g., drill holes, around the selected smallest emitting structure in the antenna substrate, e.g., metal, based on the final plurality of potential material removal points until the smallest emitting structure, e.g., fractal antennas, emit (e.g., resonate) at a first predetermined percent, e.g., five percent, under the desired frequency associated with the emitter (e.g., fractal emitter); repeat for all same sized emitting structures as the smallest emitting structure.

PROCESS FOR MANUFACTURING A PLURALITY OF WAVE ENERGY EMITTERS

CROSS-REFERENCE TO RELATED APPLICATIONS

The present application claims priority to U.S. Provisional Patent Application Ser. No. 61/713,670, filed Oct. 15, 2013, entitled "USE OF FRACTALS TO TUNE A METALLIC PLATE TO MULTIPLE RESONANCES," the disclosure of which is expressly incorporated by reference herein.

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon.

BACKGROUND AND SUMMARY OF THE INVENTION

A need exists for an emitter, e.g., a resonator, capable of resonating at multiple predefined frequencies, simultaneously having significant signal magnification capacities, increased strength, reduced weight, reduced cost, smaller form factor, elimination of need to change resonator plates to change frequencies, reduced signal reproduction degradation, and an ability to manufacture using desirable manufacturing processes and equipment. One aspect of the invention relates to a method of using fractal shapes to allow for multiple resonances in a single metallic plate for use with wavelet transforms filtered in a wavelet domain to produce or reproduce a complex waveform over a wide frequency range. Presently acoustic resonators do not exist that can, for example, resonate with a single plate, at multiple frequencies, at precise intervals such as octaves.

For example, with fractals, a prescribed magnification factor can be realized in a fractal pattern in accordance with various embodiments of the invention. Since a resonance frequency of a thin metallic circular plate is inversely proportional to a square of the diameter of the circular plate, a fractal pattern such as shown below appears to have multiple diameters, with each smaller repeated image in the fractal being reduced in size by the magnification factor of the fractal. If the magnification factor is set to the square root of two, then each successive smaller imager in the fractal will resonate at twice the frequency of the preceding larger image.

Figure 1:
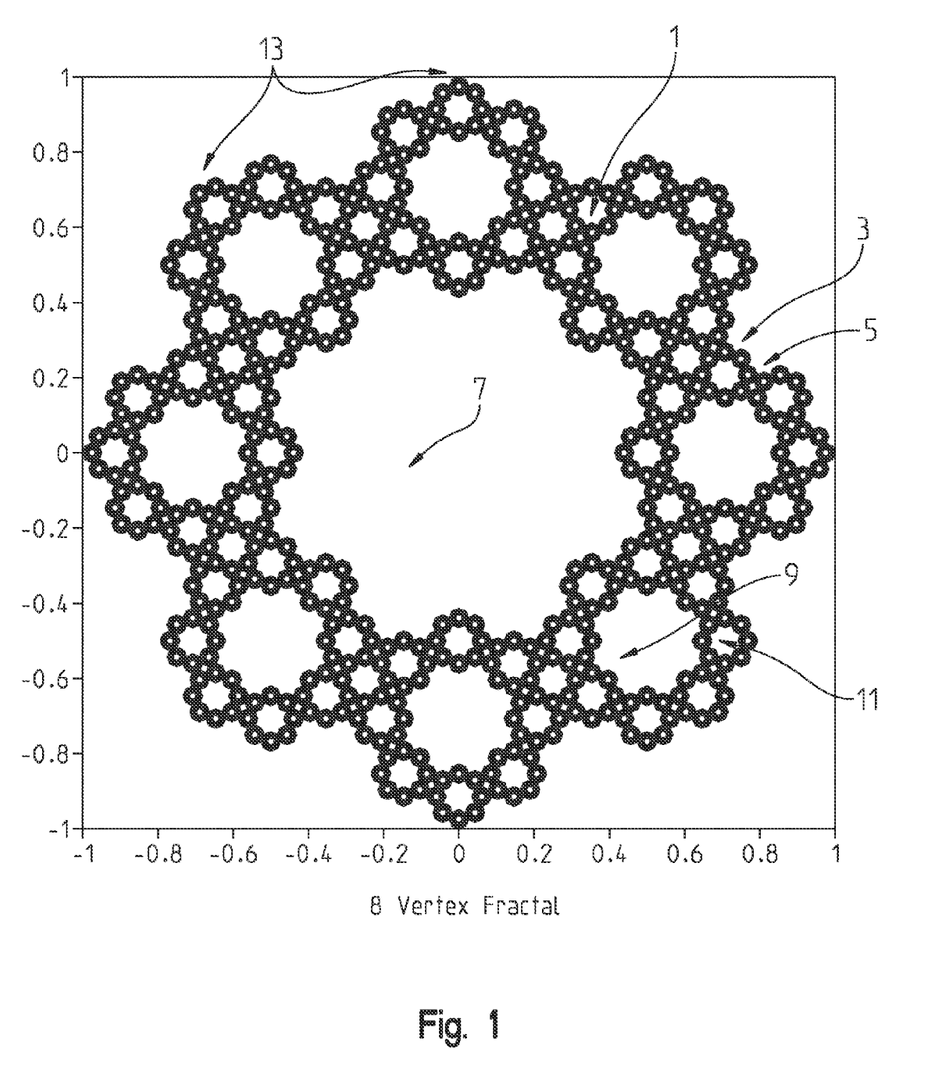
FIG. 1 shows an exemplary fractal pattern formed in a substrate which cannot provide multiple acoustic resonances while maintaining structural integrity or reproducing a signal without undesirable degradation.

According to an illustrative embodiment of the present disclosure, exemplary fractal patterns created in accordance with an embodiment of the invention can provide multiple acoustic resonances proportional to a magnification factor of a fractal. A variety of experiments demonstrated that there is significant difficulty in producing an embodiment adapted to produce results or effects associated with the invention showing that merely attempting to use a fractal design with wavelet systems did not easily result in an operable embodiment. For example, FIG. 1 shows an eight vertex fractal with the magnification factor set to the point just before overlap of the fractal images. However, this fractal could not be manufactured to create an operable result that could retain structural integrity. For example, an effort to create an embodiment using a laser to burn a hole in a thin metal disk at each point in the fractal resulted in a resulting structure that could not maintain structural integrity or reproduce a resonance signal without substantial degradation.

Figure 2:
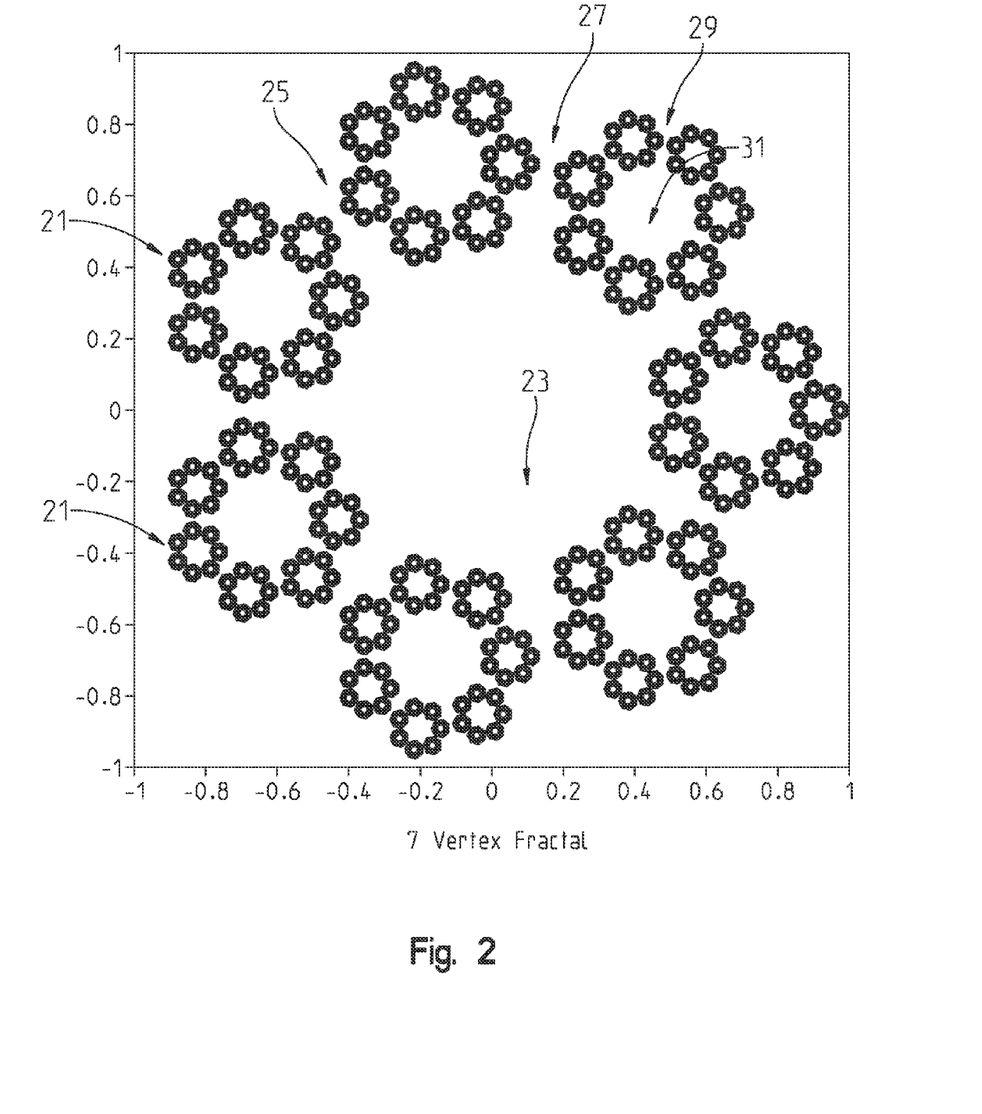
FIG. 2 shows another exemplary fractal pattern, which provides multiple acoustic resonances proportional to a magnification factor of the fractal in accordance with an embodiment of the invention with necessary structure, strength and performance characteristics.

According to a further illustrative embodiment of the present disclosure, exemplary fractal patterns provide multiple acoustic resonances proportional to the magnification factor of the fractal. For example, FIG. 2 shows a seven vertex fractal with the magnification factor set to leave some metal between successive images of the fractal pattern.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

An embodiment of the invention relates to a system and method that allows a single metallic plate to resonate at multiple frequencies. An embodiment of the invention includes an aspect for use in conjunction with wavelet transforms that allow a small set of octave tuned resonances to produce or reproduce complex time and frequency varying signals that could be focused to a small area. This highly focused sonic energy could be used for many applications such as corrosion control, non-destructive testing, motion detection, intrusion deterrent or sonic imaging to name a few.

The fractals shown in FIGS. 1 and 2 above are variations of the Sierpinski triangle with more starting vertices and varying the step to achieve a desired magnification factor such as the square root of 2 or approximately 1.4. Magnification factor can be defined as a ratio of size of one fractal image to its next smaller image. In addition to the specified magnification factor, a separation between each successive scaled replication can be incorporated so that it can be manufactured and still maintain mechanical integrity.

FIG. 1 elements 1, 3, 5, 7, 9, 11, and 13 point to a fractal antenna structure in a substrate material. The FIG. 1 dark areas are voids defined by a fractal antenna structure in a substrate material. Close proximity of the vertices defined, for example by such voids, create substantial weakness in the antenna substrate material, leading to substantial undesirable degradation and even failure. FIG. 1 antenna structures do not provide a needed separation with required structure in view of various design parameters and desired capabilities of a resulting design, however the FIG. 2 structure does.

Unlike FIG. 1, elements 21, 23, 25, 27, 29, and 31 in FIG. 2, point to connecting antenna substrate material between the first, second, and third order structures or voids that define fractal antenna elements in the substrate. Such connections provide structural integrity for the antenna. Such connections help define the fractal elements. Magnification factor and separation specified in the FIG. 2 example can be used for the purpose of use with wavelet coefficients where selected frequencies are spaced by octaves. For other uses, a different magnification factor and separation may be needed. It should be understood that various design factors used herein including, e.g., a selection of the magnification factor and separation specified herein for this example are not meant to limit the scope of this patent, but to provide an example of an application of the ideas presented in this patent. A resonate frequency of a metal plate is proportional to the thickness and inversely proportional to the square of the diameter of the plate.

Once a desired base or lowest frequency of resonance is determined, then plate thickness and diameter can be determined. A hole can be drilled (e.g., via a laser) at each point or pixel calculated by the fractal. The thickness of the plate must be selected based on the number of resonances, (scaled iterations of fractal patterns), desired and the pixel size of the penetrations into the plate. The larger the pixel size and the higher number of resonances, means a thicker plate will be needed in order to maintain mechanical strength. Assuming the smallest available pixel size, then the pixel size is no longer a variable, but a constant. Also assuming the lowest or base frequency is determined so that is no longer a variable, so the variables are thickness and diameter of the plate, number of vertices to use, number of fractal cycles or resonant frequencies and separation of fractal iterations. In this example, all of these variables are interactive and changing one forces changes in the others. For this example, in order to use with wavelets, the frequencies are separated by octaves. This means the diameter must change by the square root of 2 or 1.4 thus a magnification factor of the exemplary fractal must be 1.4. For example, if a system is desired with five resonances, such as 1 KHz, 2 KHz, 4 KHz, 8 KHz and 16 KHz and a plate material is selected i.e., aluminum, then a base frequency of 1 KHz will determine the ratio of thickness to diameter squared of the full plate. If a designer desires to create a system with five cycles of the fractal onto one plate, the resulting design will require the largest diameter as possible such that the pixel size of holes will not result in degradation of the mechanical strength of the plate at the resolution of the fifth cycle. At a smallest desired scale in this example, e.g., the 5th cycle, only an outline of a fractal pattern is drilled. In this example, after drilling the fractal pattern, the plate is pressed into a parabolic shape for focusing the sonic energy.

Figure 3A:
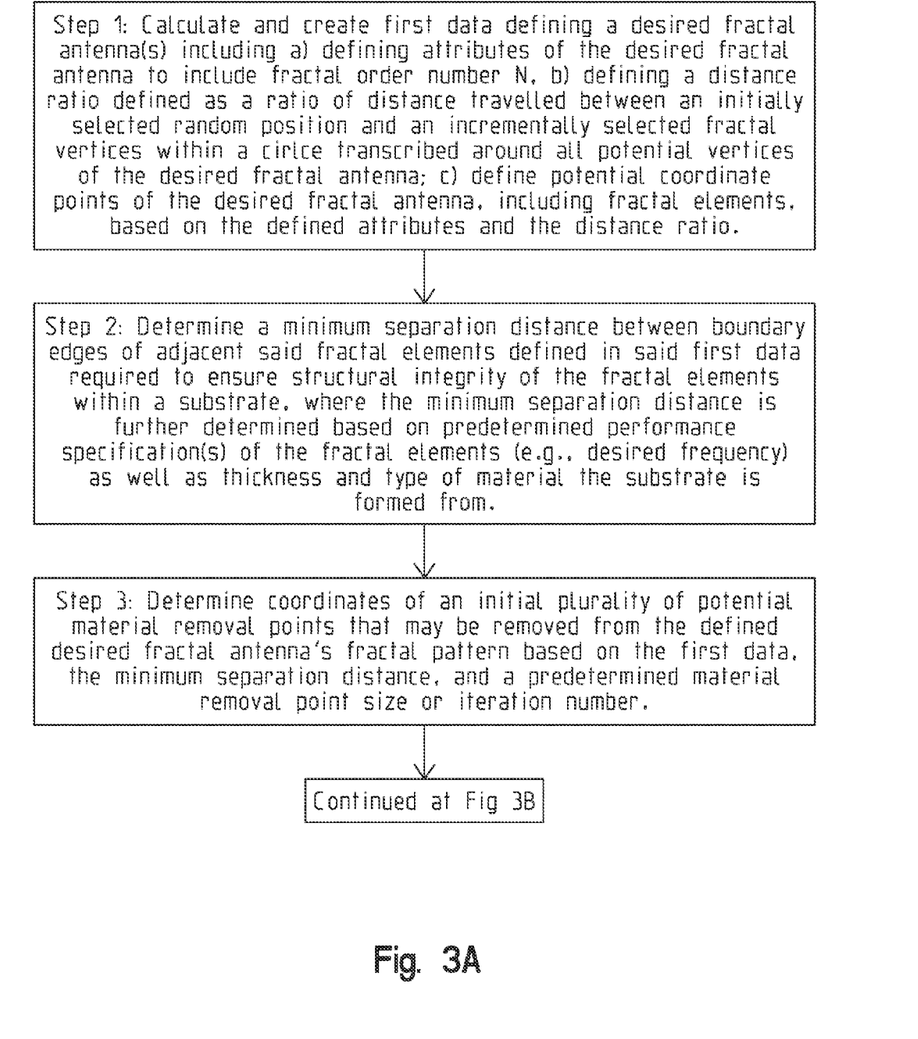
FIGS. 3A, 3B and 3C show flow chart processes of an exemplary method of manufacturing an antenna in accordance with one embodiment of the invention.
Figure 3B:
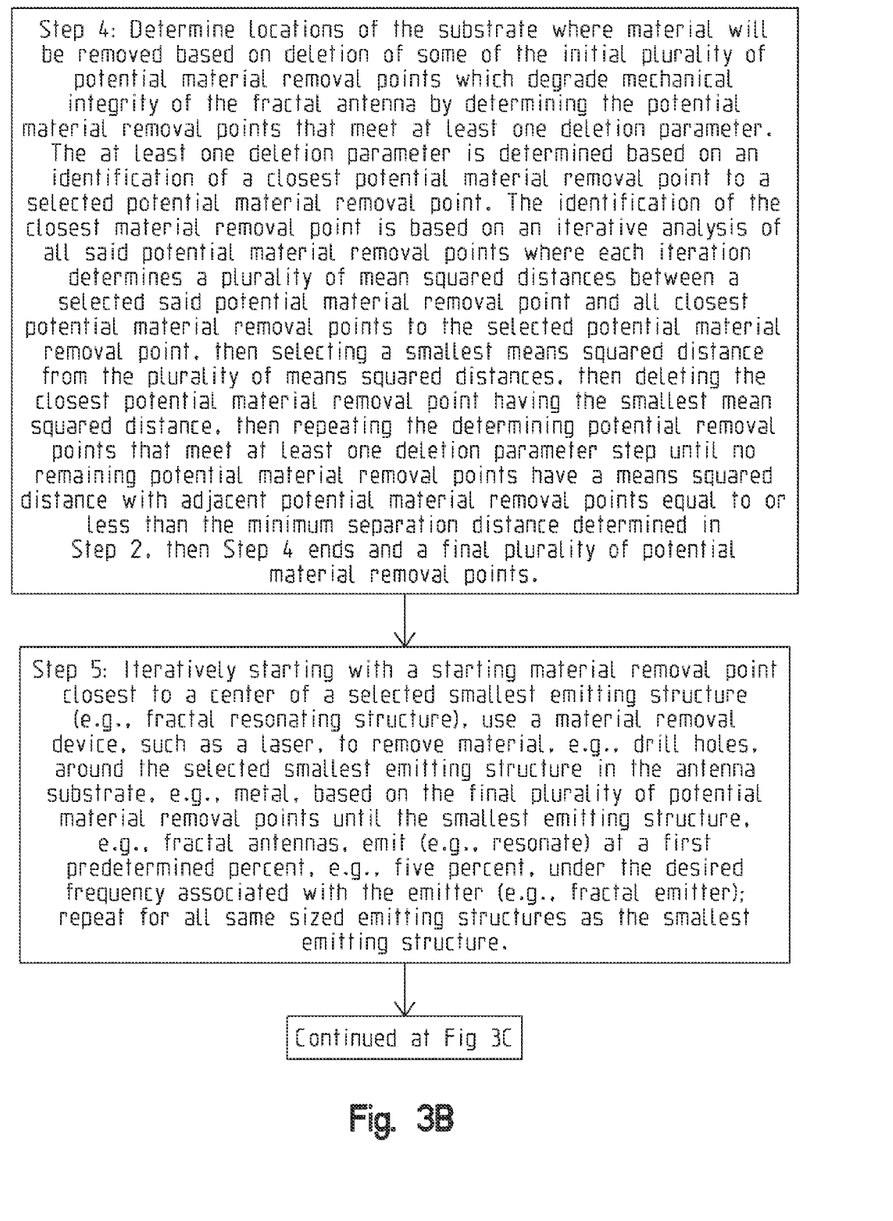

FIGS. 3A and 3B show a flow chart of an exemplary method of manufacturing a fractal antenna with satisfactory connections between fractals.

Step 1: Calculate and create first data defining a desired fractal antenna(s) comprising emitting structures comprising fractal resonating structures having fractal elements formed in or with respect to a substrate including a) defining attributes of the desired fractal antenna to include fractal order number N, b) defining a distance ratio defined as a ratio of distance traveled between an initially selected random position and an incrementally selected fractal vertices of said fractal elements within a circle transcribed around all potential vertices of the desired fractal antenna; c) define potential coordinate points of the desired fractal antenna, including fractal elements, based on the defined attributes and the distance ratio.

Step 2: Determine a minimum separation distance between boundary edges of adjacent said fractal resonating structures and said fractal elements defined in said first data required to ensure structural integrity of the fractal resonating structures and said fractal elements within said substrate, where the minimum separation distance is further determined based on predetermined performance specification(s) of the fractal elements (e.g., desired frequency) as well as thickness and type of material the substrate is formed from.

Step 3: Determine coordinates of an initial plurality of potential material removal points in said substrate that may be removed from the defined desired fractal antenna's fractal pattern based on the first data, the minimum separation distance, and a predetermined material removal point size or iteration number.

Step 4: Determine locations of the substrate where material will be removed based on deletion of some of the initial plurality of potential material removal points which degrade the structural or mechanical integrity of the desired fractal antenna by determining the potential material removal points that meet at least one deletion parameter. The at least one deletion parameter is determined based on an identification of a closest potential material removal point to each selected said potential material removal point. The identification of each closet potential material removal point to each selected said potential material removal point is based on an iterative analysis of all said potential material removal points where each iteration determines a plurality of mean squared distances between a respective said selected potential material removal point and all closest other said potential material removal points, then selecting a smallest means squared distance from the plurality of means squared distances, then deleting the closest potential material removal point having the smallest mean squared distance, then repeating the determining potential removal points that meet at least one said deletion parameter step until no remaining potential material removal points have a means squared distance with adjacent potential material removal points equal to or less than the minimum separation distance determined in Step 2, then step 4 ends and a final plurality of potential material removal points.

Step 5: Iteratively starting with a starting material removal point closest to a center of a selected smallest emitting structure (e.g., fractal resonating structure) amongst said final plurality to potential material removal points, use a material removal device, such as a laser, to remove material from the substrate, e.g., drill holes, around the selected smallest emitting structure in the antenna substrate, e.g., metal, based on the final plurality of potential material removal points until the smallest emitting structure, e.g., fractal antenna[s], emit (e.g., resonate) at a first predetermined percent, e.g., five percent, under each desired frequency associated with each associated emitter (e.g., fractal emitter); repeat for all same sized emitting structures as the smallest emitting structure.

Figure 3C:
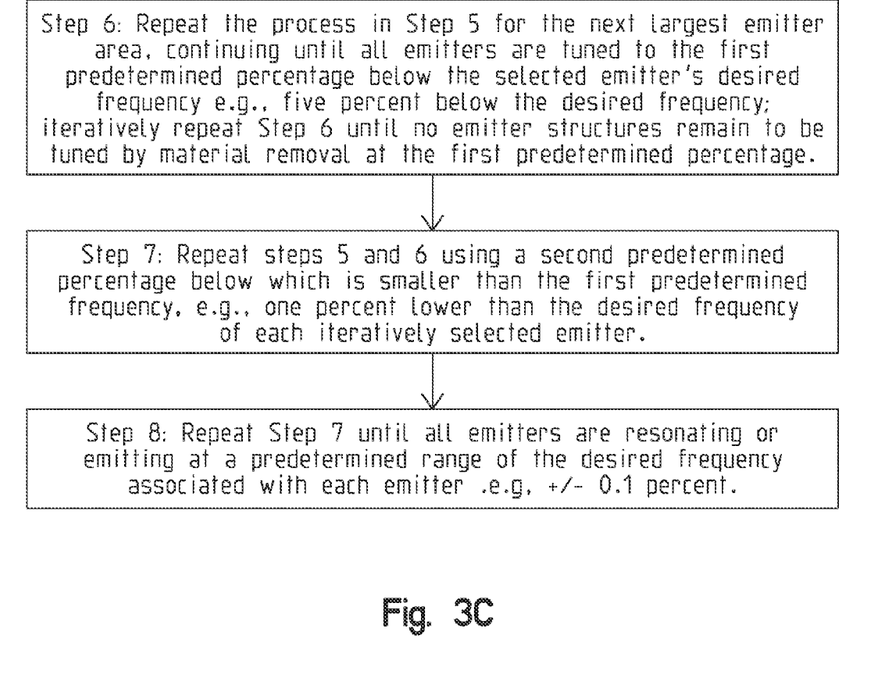

Step 6: Repeat the process in Step 5 for each said emitter structure in sequence selecting based on next largest emitter area, continuing until all of the emitters are designed to be tuned to their associated said first predetermined percentage below each respective said selected emitter's or fractal resonating structure's desired frequency e.g., five percent below the respective desired frequency; iteratively repeat Step 6 until no emitter structures remain to be tuned by material removal at the first predetermined percentage.

Step 7: Repeat steps 5 and 6 using successive different associated second predetermined percentage which is smaller than the first predetermined frequency, e.g., one percent lower than the desired frequency of each iteratively selected emitter.

Step 8: Repeat Step 7 until all emitters are designed for resonating or emitting at a predetermined range of the desired frequency associated with each emitter, e.g, +/−0.1 percent.

Figure 4:
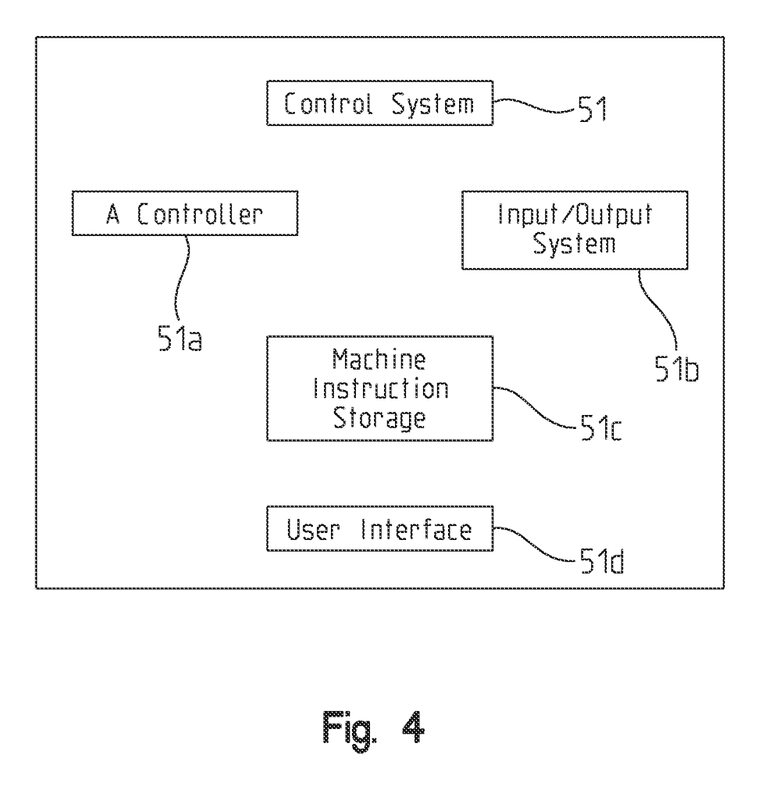
FIG. 4 shows a block diagram of an exemplary system in accordance with one embodiment of the invention.

FIG. 4 shows a diagram of an exemplary control system 51 in accordance with one embodiment of the invention. The FIG. 4 exemplary system is comprised of a controller 51a, an input/output system 51b, a machine instruction storage 51c, and a user interface processing software (e.g., that applies the method of manufacturing in FIG. 3) 51d.

Figure 5:
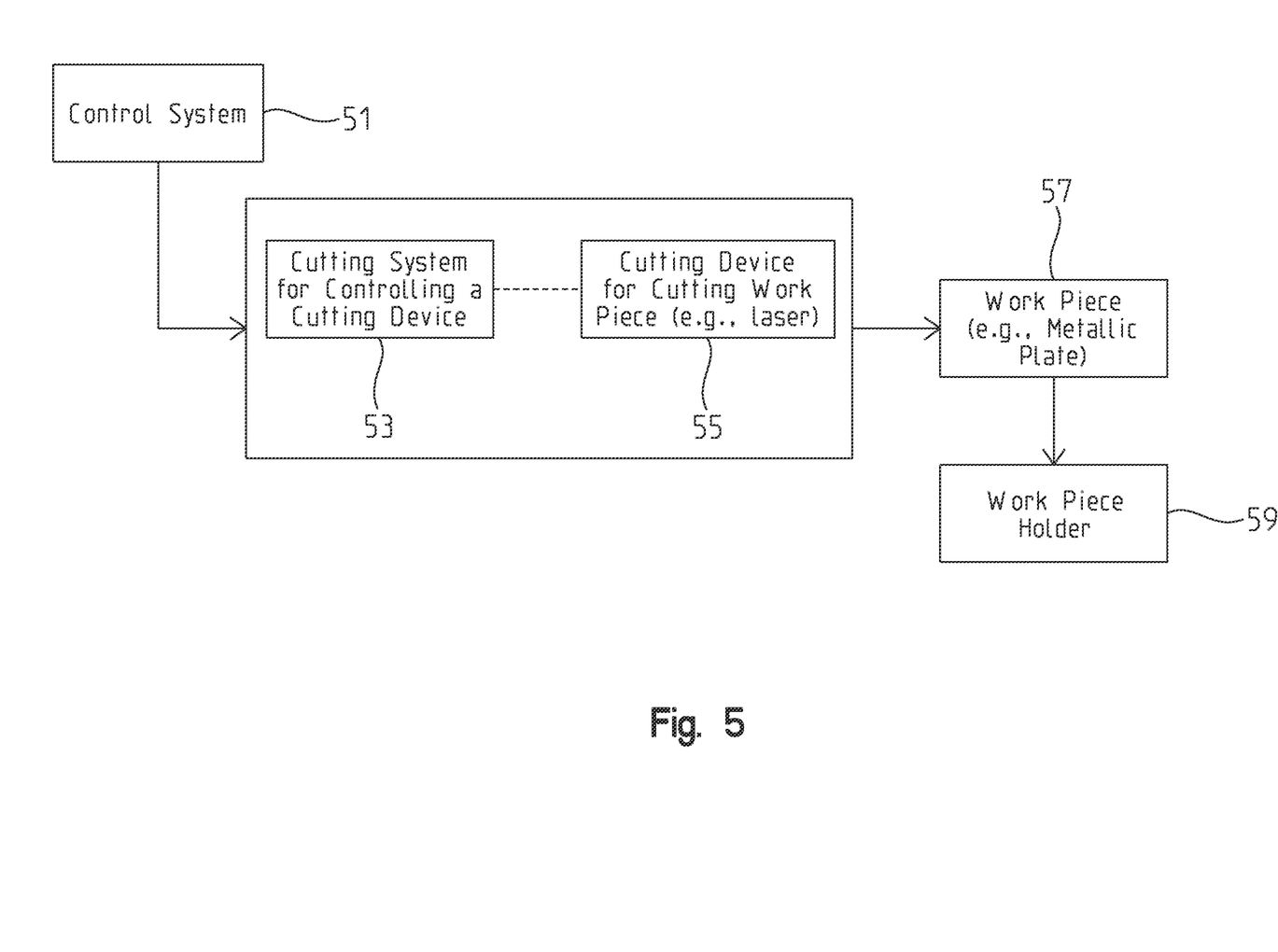
FIG. 5 shows another block diagram of an exemplary system in accordance with an embodiment of the invention.

FIG. 5 shows a system to manufacture fractal antennas in accordance with one embodiment of the invention. The system is comprised of a control system 51, a cutting system for controlling a cutting device 53, a device for cutting the work piece (e.g. a laser) 55, a work piece (i.e. metallic plate) 57, and a work piece holder 59.

A fractal antenna is a product produced by a manufacturing process comprising, for example, Steps 1-9 as show in FIG. 3 or with an apparatus described in FIGS. 4 and 5 with elements 51, 51a, 51b, 51c, 51d, 53, 55, 57, and 59.

Although the invention has been described in detail with reference to certain preferred embodiments, variations and modifications exist within the spirit and scope of the invention as described and defined in the following claims.

The invention claimed is:

1. A process for manufacturing a plurality of wave energy emitters in an emitter assembly or structure comprising:
   executing a first process step comprising calculating and creating a first data defining a desired fractal antenna comprising fractal resonating structures having fractal elements formed in a substrate including:
      defining attributes of the desired fractal antenna comprising the fractal elements to include fractal order number N;
      defining a distance ratio defined as a ratio of distance traveled between an initially selected random position and an incrementally selected fractal vertices of said fractal elements within a circle transcribed around all potential vertices of the desired fractal antenna; and
      defining potential coordinate points defining the desired fractal antenna in said substrate based on the defined attributes and the distance ratio;
   executing a second process step comprising determining a minimum separation distance between boundary edges of adjacent said fractal resonating structures and fractal elements defined in said first data required to ensure structural integrity of the fractal resonating structures and fractal elements within said substrate is maintained, wherein the minimum separation distance is further determined based on a predetermined performance specification of the fractal resonating structures and the fractal elements comprising desired frequencies associated with each resonating structures and related fractal element as well as thickness and type of material the substrate is formed from;
   executing a third process step determining coordinates of an initial plurality of potential material removal points in said substrate that may be removed from the defined said desired fractal antenna's fractal pattern based on the first data, the minimum separation distance, and a predetermined material removal point size or iteration number;
   executing a fourth process step comprising determining locations of the substrate where substrate material will be removed based on deletion of some of the initial plurality of potential material removal points which degrade said structural or mechanical integrity of the desired fractal antenna by determining the potential material removal points that meet at least one deletion parameter, the at least one deletion parameter is determined based on an identification of a closest potential material removal point to one or more selected said potential material removal point, the identification of the closet material removal point is further based on an iterative analysis of all said potential material removal points where each iteration determines a plurality of mean squared distances between each respective said selected potential material removal points and all closest other said potential material removal points to the respective said selected potential material removal point, then selecting a smallest means squared distance from the plurality of means squared distances then deleting the closest potential material removal point having said smallest mean squared distance, then repeating the step of determining potential removal points that meet at least one said deletion parameter step until no remaining potential material removal points have a means squared distance with adjacent potential material removal points equal to or less than the minimum separation distance previously determined to produce a final plurality of potential material removal points;
   executing a fifth process step comprising iteratively starting with a starting material removal point closest to a center of a selected smallest emitting structure comprising one of said fractal resonating structures amongst said final plurality of potential material points, using a material removal device to remove material from the substrate around the selected smallest emitting structure in the antenna substrate based on the final plurality of potential material removal points until the smallest emitting structure comprising the fractal antennas, emit or resonate at a first predetermined percent of under each desired frequency associated with each associated emitter; repeat for all same sized emitting structures as the smallest emitting structure;
   executing a sixth process step comprising repeating the process step at the fifth process step for a next largest emitter area, continuing until all of the emitters are designed to be tuned to their associated said first predetermined percentage below respective said selected fractal resonating structure's desired frequency percentage increment below an associated said desired frequency, then iteratively repeating the sixth process step until no said emitter or fractal resonating structures comprising said fractal elements remain to be tuned by material removal at each said first predetermined percentage;
   executing a seventh process step comprising repeating the fifth and sixth process steps using successive different associated second predetermined percentages which are smaller than iteratively selected said first predetermined frequency percentage lower than the desired frequency of each iteratively selected emitter comprising said fractal resonating structure and fractal elements;
   repeating said seventh process step until all said emitters comprising said fractal resonating structures and related fractal elements are determined for resonating or emitting at a predetermined range of the desired frequency associated with each emitter within a predetermined plus or minus percentage.

2. A process as in claim 1, wherein said material removal device comprises a laser, drill, or another cutting device.

3. A process as in claim 1, wherein said second predetermined percentage that is smaller than the first predetermined frequency percentage comprises one percent lower than the desired frequency of each iteratively selected emitter.

4. A process as in claim 1, wherein said first predetermined percentage below the selected emitter's desired frequency comprises five percent below the desired frequency.

5. A process as in claim 1, wherein said substrate comprises a metal.

6. A process as in claim 1, wherein said predetermined plus or minus percentage comprises +/−0.1 percent.

7. A process as in claim 1, wherein at least some of said each associated emitter comprise a fractal emitter.

* * * * *